US00PP19577P2

(12) United States Plant Patent
Delabroye

(10) Patent No.: US PP19,577 P2
(45) Date of Patent: Dec. 16, 2008

(54) ***HEUCHERA* PLANT NAMED 'BEAUJOLAIS'**

(50) Latin Name: *Heuchera*
Varietal Denomination: Beaujolais

(76) Inventor: Sandrine Delabroye, Rue Roger Satengro 40, Hantay (FR), F-59496

( * ) Notice: Subject to any disclaimer, the term of this patent is extended or adjusted under 35 U.S.C. 154(b) by 0 days.

(21) Appl. No.: 12/008,338

(22) Filed: Jan. 10, 2008

(51) Int. Cl.
*A01H 5/00* (2006.01)

(52) U.S. Cl. ..... Plt./440

(58) Field of Classification Search ..... Plt./440
See application file for complete search history.

*Primary Examiner*—Annette H Para
*Assistant Examiner*—S. B. McCormick-Ewoldt
(74) *Attorney, Agent, or Firm*—Penny J. Aguirre

(57) ABSTRACT

A new cultivar of *Heuchera* of hybrid origin, 'Beaujolais', characterized by its relatively large, orbicular shaped leaves that are dark burgundy red in color with silver highlights and darker burgundy red veins held on burgundy red petioles. 'Beaujolais' is further characterized by its low mounded and compact plant habit, its tolerance to high heat and humidity, and its hardiness in U.S.D.A. Zones 4 to 9.

2 Drawing Sheets

Botanical classification: *Heuchera* hybrid.
Cultivar designation: 'Beaujolais'.

CROSS REFERENCE TO A RELATED APPLICATION

This application is co-pending with U.S. Plant Patent applications filed for sibling plants derived from the same cross in the inventor's breeding program that are entitled *Heuchera* Plant Named 'Pinot Noir' (U.S. Plant Patent application Ser. No. 12/002,889), *Heuchera* Plant Named 'Encore' (U.S. Plant Patent application Ser. No. 12/008,941), *Heuchera* Plant Named 'Pinot Gris' (U.S. Plant Patent application Ser. No. 12/008,928), *Heuchera* Plant Named 'Tiramisu' (U.S. Plant Patent application Ser. No. 12/002,921), and Heuchera Plant Named 'Pistache' (U.S. Plant Patent application Ser. No. 12/008,927).

BACKGROUND OF THE INVENTION

The present invention relates to a new and distinct cultivar of hybrid *Heuchera,* botanically known as a *Heuchera* of hybrid origin and is hereinafter referred to by the cultivar name 'Beaujolais'.

The new cultivar was derived from a controlled breeding program by the inventor in Hantay, France. The inventor made a cross in summer of 2005 between *Heuchera* 'Gloire d'Orleans' (not patented, syn. *Heuchera*×*brizodes* 'Gloire d'Orleans') and *Heuchera*×*villosa* 'Caramel' (U.S. Plant Pat. No. 16,560). The goal of the breeding program was to obtain unique cultivars of *Heuchera* that combined the flowering habit of 'Gloire d'Orleans' with the vigor and unique foliage coloration of *Heuchera*×*villosa.* The inventor selected 'Beaujolais' in 2006 as a single unique plant amongst the seedlings that resulted from the above cross.

Asexual reproduction of the new cultivar was first accomplished under direction of the inventor by in vitro propagation in Rijswijk, The Netherlands in winter of 2007. Asexual reproduction of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Beaujolais' as a new and unique cultivar of *Heuchera.*

1. 'Beaujolais' exhibits unique foliage with leaves that are dark burgundy red in color with silver highlights and darker burgundy red veins, leaves are held on purple petioles.
2. 'Beaujolais' exhibits large, orbicular shaped leaves.
3. 'Beaujolais' exhibits a compact, low mounding plant habit.
4. 'Beaujolais' is tolerant to high heat and humidity imparted by having *Heuchera*×*villosa* in its parentage.
5. 'Beaujolais' is cold hardy in U.S.D.A. Zones 4 to 9.

'Beaujolais' is a unique *Heuchera* with more vigor, cold hardiness, and tolerance to heat and humidity than is typical for a red foliaged *Heuchera.* 'Beaujolais' differs from its parent plants in that 'Caramel' is a ×*villosa* hybrid and has foliage that is yellow-orange in color and 'Gloire d'Orleans' is a ×*brizoides* hybrid with green foliage.

'Beaujolais' can be compared to *Heuchera* 'Plum Pudding' (not patented) for its similar leaf color, however 'Plum Pudding' has smaller ovate shaped leaves that are ruffled and more purple in color and 'Plum Pudding' exhibits more rounded plant habit. The closest comparison plants in overall leaf shape, habit, and performance are its sibling cultivars that differ in foliage coloration; 'Pinot Noir' has dark purple-grey leaves, 'Encore' has rose-purple leaves, 'Pinot Gris' has leaves that emerge orange-yellow and mature to a rose color with a silvery overlay, 'Tiramisu' has foliage that is yellow-green with red mottling, and 'Pistache' has yellow-green leaves.

BRIEF DESCRIPTION OF THE DRAWING

The accompanying colored photographs illustrate the overall appearance and distinct characteristics of the new *Heuchera.* The photographs were taken in mid summer of plants six months in age as grown outdoors in a trial garden in The Netherlands.

The photograph on the first sheet provides a view of the plant habit and typical mid summer coloration of the new and mature foliage.

The photograph on the second sheet provides a close-up view of a leaf of 'Beaujolais'.

The colors in the photographs are as close as possible with the photographic and printing technology utilized. The color values cited in the detailed botanical description accurately describe the colors of the new *Heuchera*.

DETAILED BOTANICAL DESCRIPTION OF THE PLANT

The following is a detailed description of six month-old plants of the new cultivar as grown in a 2-liter container outdoors in The Netherlands. Plants were grown under average day temperatures of 12° to 30° C. and average night temperatures of 5° to 16° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Plant habit.*—Compact, low mounding, herbaceous perennial.

*Height and spread.*—Reaches a height of about 13.5 cm and a width of about 39 cm.

*Hardiness.*—At least hardy to U.S.D.A. Zone 4 to 9.

*Culture.*—Full sun to medium shade in moist, well-drained, fertile soils, tolerant to high heat and humidity.

*Diseases and pests.*—Disease free in the conditions tested, no susceptibility or resistance to pests has been observed.

*Root description.*—Fibrous roots on woody rootstalks.

*Branching habit.*—Basal rosettes of leaves on petioles.

*Propagation.*—In vitro propagation is the preferred method, division are also possible.

*Root initiation.*—Roots appear in rooting media in 10 day at 20° C. in the laboratory without supplemental lighting.

*Root development.*—Rooted transplants from tissue culture fully develop in a 2.5 inch container in about 20 days in a greenhouse with average temperatures of about 20° C. without supplemental lighting in The Netherlands.

*Growth rate.*—Moderately vigorous, growth rate in spring is 5 cm per month in The Netherlands.

Foliage Description:

*Leaf shape.*—Orbicular.

*Leaf division.*—Simple.

*Leaf base.*—Reniform, moderately overlapping.

*Leaf apex.*—Rounded with a very small (0.5 mm) abruptly acute tip.

*Leaf venation.*—Primary palmate, secondary net-veined, conspicuous, color on upper surface is between 177D and 182D and flushed with 152D, color on lower surface 187A.

*Leaf margins.*—Lobed with average of 7 lobes per leaf, lobes are crenate with very small abruptly acute tips.

*Leaf attachment.*—Petiolate.

*Leaf arrangement.*—Basal rosettes.

*Leaf orientation.*—Held upright to horizontal to petiole, nearly flat (not ruffled or curled).

*Leaf surface.*—Upper surface; dull, slightly rough to touch, pubescent with white hairs 0.5 mm in length; 155C, margins; moderately pubescent, average length of hairs 0.3 mm in length, N155D to 186D, lower surface; moderately covered with short hairs, average of 0.7 mm in length, 155C.

*Leaf color.*—Young upper surface; between 177D and 182D between veins, young lower surface; 59A to 187A to 187B, mature upper surface; between 177D and 182D between veins but slightly lighter than the young leaf color with darker areas near veins and margins; 176A, mature lower surface; 59A to 187A.

*Leaf size.*—Average of 11.9 cm in length and 11 cm in width.

*Leaf quantity.*—About 40 per basal rosette.

*Petioles.*—Average of 9.5 cm in length and 3 mm in width, 59A to 187A in color, round in shape, surface is densely pubescent with short hairs, average of 1 mm in length and 155D in color.

*Stipules.*—None.

Flower and seed description: Flowering has not been observed under the conditions grown for data collection, white bell-shaped flowers larger than typical of the species should be expected under the right conditions for flowering, no seeds have been observed.

It is claimed:

1. A new and distinct cultivar of *Heuchera* plant named 'Beaujolais' as herein illustrated and described.

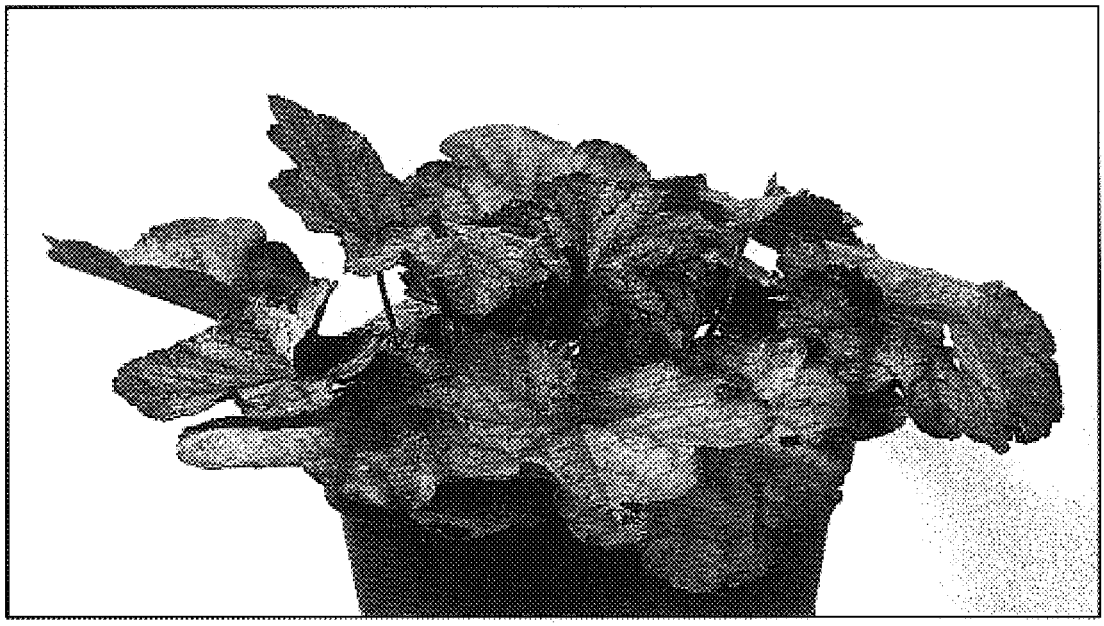

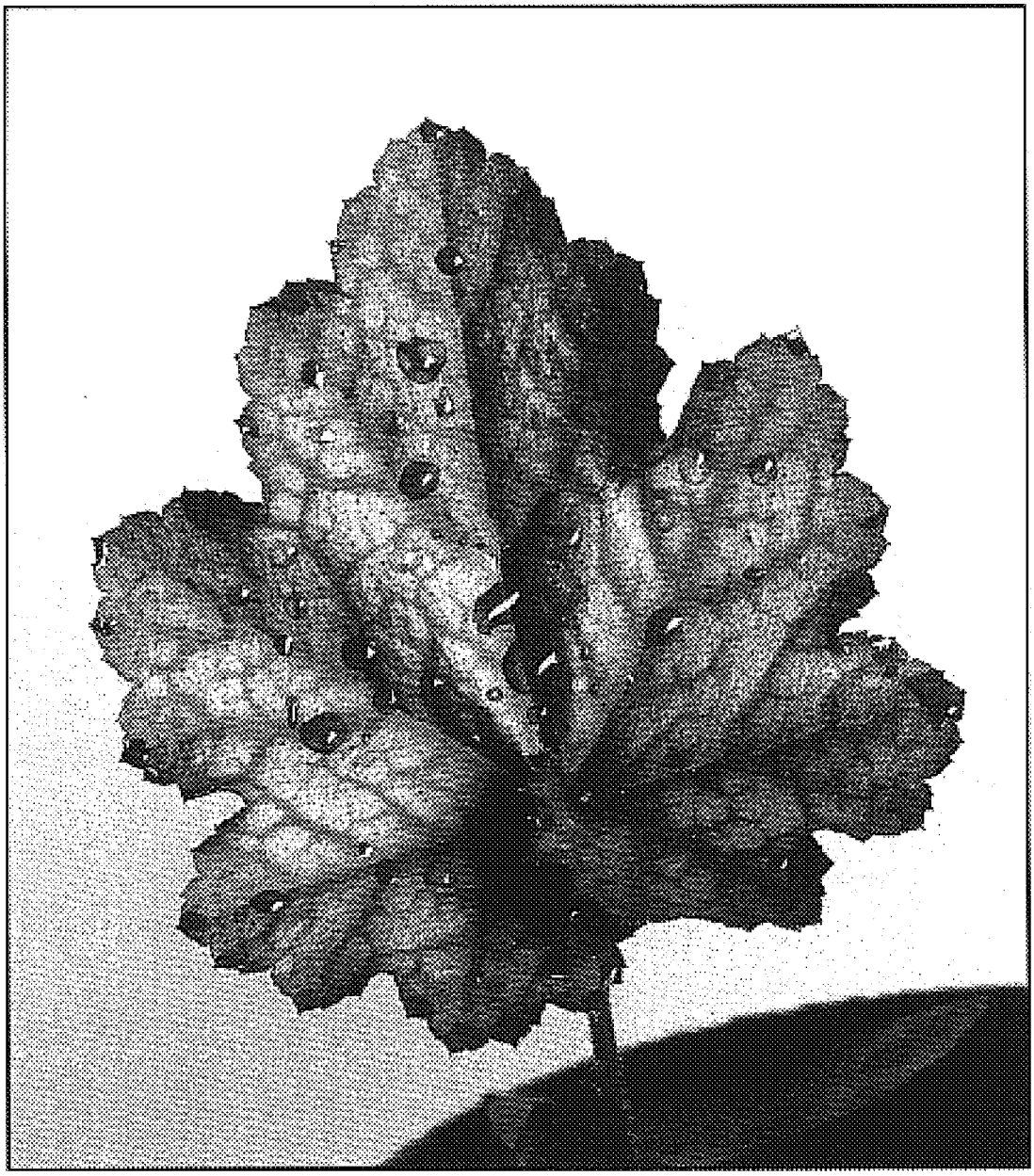

* * * * *